United States Patent
Moser et al.

(10) Patent No.: US 9,498,340 B2
(45) Date of Patent: *Nov. 22, 2016

(54) BLADE-LIKE STEM OF A HIP-JOINT PROSTHESIS

(75) Inventors: Walter Moser, Kaufdorf (CH); Alex Seidl, Zürich (CH); Dirk Wunderle, Zürich (CH)

(73) Assignee: Smith & Nephew Orthopaedics AG, Rotkreuz (CH)

( * ) Notice: Subject to any disclaimer, the term of this patent is extended or adjusted under 35 U.S.C. 154(b) by 769 days.

This patent is subject to a terminal disclaimer.

(21) Appl. No.: 12/067,635

(22) PCT Filed: Aug. 8, 2006

(86) PCT No.: PCT/EP2006/007842
§ 371 (c)(1),
(2), (4) Date: Oct. 15, 2008

(87) PCT Pub. No.: WO2007/033727
PCT Pub. Date: Mar. 29, 2007

(65) Prior Publication Data
US 2009/0036994 A1 Feb. 5, 2009

(30) Foreign Application Priority Data

Sep. 20, 2005 (DE) .................. 10 2005 044 872
Oct. 12, 2005 (DE) .................. 10 2005 048 873

(51) Int. Cl.
*A61F 2/36* (2006.01)
*A61F 2/30* (2006.01)
*A61F 2/46* (2006.01)

(52) U.S. Cl.
CPC .............. *A61F 2/3662* (2013.01); *A61F 2/36* (2013.01); *A61F 2/367* (2013.01); *A61F 2/3676* (2013.01); *A61F 2002/30148* (2013.01); *A61F 2002/30151* (2013.01); *A61F 2002/30153* (2013.01); *A61F 2002/30158* (2013.01);
(Continued)

(58) Field of Classification Search
USPC ............. 623/22.11, 22.4–22.4, 23.15, 23.18, 623/23.23–23.26, 23.28–23.29, 623/23.34–23.353
See application file for complete search history.

(56) References Cited

U.S. PATENT DOCUMENTS 4,279,042 A * 7/1981 Andriacchi et al. ........ 623/23.15
4,310,931 A * 1/1982 Muller ......................... 623/22.4
(Continued)

FOREIGN PATENT DOCUMENTS

| EP | 0032165 A2 | 7/1981 |
|---|---|---|
| EP | 0145939 A2 | 6/1985 |
| FR | 2678510 A | 1/1993 |

OTHER PUBLICATIONS

English Translation of International Preliminary Report on Patentability for PCT/EP2006/007842, mailed Apr. 8, 2008.
(Continued)

*Primary Examiner* — Marcia Watkins
(74) *Attorney, Agent, or Firm* — Taft Stettinius & Hollister LLP

(57) ABSTRACT

A blade-like stem of a hip joint prosthesis for anchoring in the femur, including a portion comprising a prosthesis neck on the one hand and a femur-anchoring portion tapering towards a distal end on the other hand, the lateral narrow side of which comprises a distal straight portion and a proximal arcuate portion, the straight portion extending over a length of from 60% to 75% of the total length of the stem.

37 Claims, 5 Drawing Sheets

(52) U.S. Cl.
CPC .............. *A61F 2002/30205* (2013.01); *A61F 2002/30253* (2013.01); *A61F 2002/30255* (2013.01); *A61F 2002/30257* (2013.01); *A61F 2002/30332* (2013.01); *A61F 2002/30606* (2013.01); *A61F 2002/30616* (2013.01); *A61F 2002/30785* (2013.01); *A61F 2002/30795* (2013.01); *A61F 2002/365* (2013.01); *A61F 2002/368* (2013.01); *A61F 2002/3625* (2013.01); *A61F 2002/4631* (2013.01); *A61F 2002/4635* (2013.01); *A61F 2220/0033* (2013.01); *A61F 2230/008* (2013.01); *A61F 2230/0017* (2013.01); *A61F 2230/0019* (2013.01); *A61F 2230/0026* (2013.01); *A61F 2230/0067* (2013.01); *A61F 2230/0076* (2013.01); *A61F 2230/0078* (2013.01)

(56) References Cited

U.S. PATENT DOCUMENTS

| | | | |
|---|---|---|---|
| 4,404,693 A | | 9/1983 | Zweymuller |
| 4,753,657 A | * | 6/1988 | Lee et al. ............... 623/16.11 |
| 5,888,210 A | * | 3/1999 | Draenert ................ 623/23.35 |
| 6,168,632 B1 | * | 1/2001 | Moser et al. ............ 623/23.31 |
| 6,540,788 B1 | | 4/2003 | Zweymuller |
| 6,613,094 B2 | | 9/2003 | Zweymuller |
| 6,808,539 B2 | | 10/2004 | Zweymuller |
| 7,004,973 B2 | | 2/2006 | Zweymuller |
| 7,175,668 B2 | | 2/2007 | Zweymuller |
| 7,749,278 B2 | * | 7/2010 | Frederick et al. ......... 623/22.41 |
| 2005/0055103 A1 | * | 3/2005 | Badatcheff et al. ....... 623/22.42 |
| 2005/0267586 A1 | * | 12/2005 | Sidebotham ............. 623/22.41 |
| 2006/0206212 A1 | | 9/2006 | Zweymuller |
| 2006/0276904 A1 | | 12/2006 | Zweymuller |

OTHER PUBLICATIONS

U.S. Appl. No. 09/958,463, filed Apr. 9, 2002, Zweymuller.
English Translation of Notification of Reasons for Rejection regarding counterpart Japanese Patent Application No. 2008-530349, May 25, 2011, Japanese Patent Office.
Canadian Office Action; Canadian Intellectual Property Office; Canadian Patent Application No. 2,622,010; Oct. 17, 2012; 2 pages.

* cited by examiner

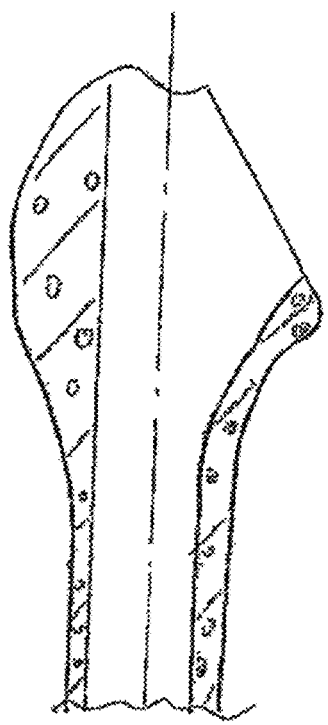 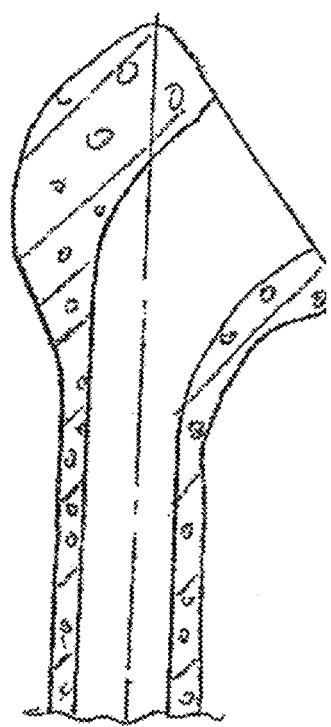
FIG. 4
Prior Art
FIG. 5

BLADE-LIKE STEM OF A HIP-JOINT PROSTHESIS

CROSS-REFERENCE TO RELATED APPLICATIONS

This Application is a US National Phase of the International Application No. PCT/EP2006/007842 filed Aug. 8, 2006 designating the US and published in German on Mar. 29, 2007 as WO 2007/033727, which claims priority of German Patent Application No. 10 2005 044 872.0, filed Sep. 20, 2005, as well as German Patent Application No. 10 2005 048 873.0, filed Oct. 12, 2005.

BACKGROUND OF THE INVENTION

1. Field of the Invention

The invention relates to a blade-like stem of a hip joint prosthesis for anchoring in the femur, having a portion comprising a prosthesis neck on the one hand and a femur-anchoring portion tapering towards a distal end on the other hand.

2. Description of the Related Art

A blade-like stem generally known in the art is described in EP 0 240 815 B1. A stem corresponding generally to FIG. 6 is shown and described therein. Accordingly, that stem 1 comprises a portion comprising a prosthesis neck 7 on the one hand and a femur-anchoring portion 2 tapering towards a distal end 3 on the other hand. That femur-anchoring portion widens conically all around from the distal end 3 in the direction of the stem longitudinal axis 4. The medial narrow side 5 merges out of the said cone into a continuously curved arc which ends in a plane which, running perpendicular to the prosthesis neck axis 6, terminates the prosthesis neck 7 towards the stem blade, i.e. the femur-anchoring portion 2. The prosthesis neck 7 ends in an outwardly conically tapering pin on which a spherical joint head (not shown) can be placed.

The lateral narrow side 8 widens out of the conical widened portion to form a trochanter wing 9 before merging, via a shoulder of the stem blade or anchoring portion, into the said prosthesis neck termination plane.

In both cases, a stem-receiving space, that is to say a corresponding cavity, has to be provided beforehand in the femur, that being effected by means of a shaping instrument, especially a rasp, corresponding to the shape of the stem. Such shaping instruments or rasps correspond exactly to the geometry of the stem in question or differ specifically therefrom in order to obtain a predetermined undersize for a press-fit or a predetermined oversize as space for a cement mantle.

Once the hip joint has been opened and the neck of the femur resectioned, in the proximal femur the bony bearing is prepared for receiving the anchoring stem. According to the shape of the stem, the bony anchoring bed is created using a suitable shaping instrument, especially a rasp, by movement down along the stem axis. For moving down into the medullary space, which is filled with spongy bone and soft tissue, the rasp is driven forwards by means of a weight acting as a hammer or using some other suitable instrument. In the case of a curved stem axis, the shaping instrument or rasp is moved down in an arc along a curved path, while in the case of a straight stem axis the rasp is driven forward along a straight line corresponding substantially to the axis of the proximal medullary space.

For cementless anchoring of hip stems, the configuration of the anchoring portion as a straight stem has proved especially suitable clinically. This concept allows a secure implantation technique, high primary stability and good ingrowth behaviour. The current surgical techniques for such stems generally require the medullary space to be opened not only in the plane of the resection surface of the neck of the femur, but also further laterally into the region of the greater trochanter. Reference is made in this respect to FIG. 4. That Figure shows that a resection of portions of the tendon insertions in that region is also generally necessary. The extent of that resection of course depends upon the individual shape of the proximal femur and upon the shaping of the straight stem, among other things.

More recently, there has been an increase in implantations of joint endoprostheses carried out using minimally invasive surgical techniques. The aim of such techniques is more rapid rehabilitation of the patient, which is associated with a reduction in pain and a shorter stay in hospital. Minimally invasive surgical techniques keep operative trauma, especially in respect of the functionally significant structures, to a very low level. For the functioning of the hip joint the important structural features are the muscles and tendons. The aim of minimally invasive implantation techniques is inter alia to avoid resections and detachments of tendon and muscle insertions in the region of the greater trochanter. Classic straight stems accordingly have disadvantages for the use of minimally invasive techniques.

To avoid resections in the region of the tendon insertions on the greater trochanter, in the case of straight stems the lateral area can be chamfered in the region of the trochanter. Straight stems having a flattened shoulder have been proposed. An example is the so-called Müller straight stem shown and described in "Technique d'implantation de prothèses totales de Müller par voie latérale transglutéale", Encyclopédie Medico-Chirurgicale (Paris) 44666, 1991.

The aim of that flattened shoulder is to avoid major defects in the region of the ridge of the trochanter. When shaping that flattened portion, a proportion of the lateral stem area, which proportion is constant within the size system, was generally configured with straight shaping inclined relative to the stem axis or with a radius. The rasp corresponding to the implant was generally made geometrically identical to the implant. From the technical standpoint, the rasp is used to create an undercut in the region of the greater trochanter, as can be seen in FIG. 5.

In the case of implantation of a hip stem, the bony bed is shaped using rasps of increasing size up to the size giving the best fit, the rasp in question following the shape of the existing bed formed by the preceding rasp size. Because the distal portion of the straight stem is effected by moving down along a straight axis, compromises are made in terms of exact fit in respect of the inclined or curved shoulder area. That is influenced, however, by the surgeon's rasp technique and individual bone quality.

SUMMARY OF THE INVENTION

The present invention, described below, comprises a stem typically used for cementless anchoring in the femur. In principle, however, the present invention described below is intended to relate also, for example, to cemented stems as well as other stems.

Improving upon the above-mentioned prior art, one aim of the present invention is to provide a blade-like stem of the kind mentioned at the beginning that is especially suitable for minimally invasive surgical techniques. In so doing, the advantages of conventional straight stem implants generally should be retained, but muscle and tendon insertions should be protected as much as possible.

That problem is solved according to one embodiment of the invention as follows: the lateral narrow side of the stem comprises a distal straight portion and a proximal arcuate portion, the straight portion extending over a length of from 60% to 75% of the total length of the stem.

BRIEF DESCRIPTION OF THE DRAWINGS

FIG. 4 depicts a resected bone for insertion of a straight stem prosthesis;

FIG. 5 depicts a resected bode with an undercut, for insertion of a prosthesis;

DETAILED DESCRIPTION OF THE PREFERRED EMBODIMENTS

Figure 1:
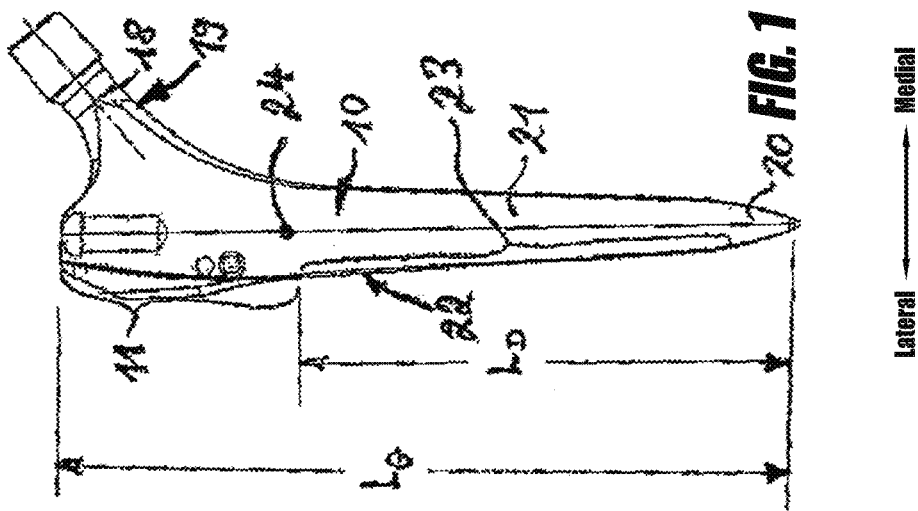
FIG. 1 depicts a schematic side view of one embodiment of a hip joint prosthesis.
Figure 2:
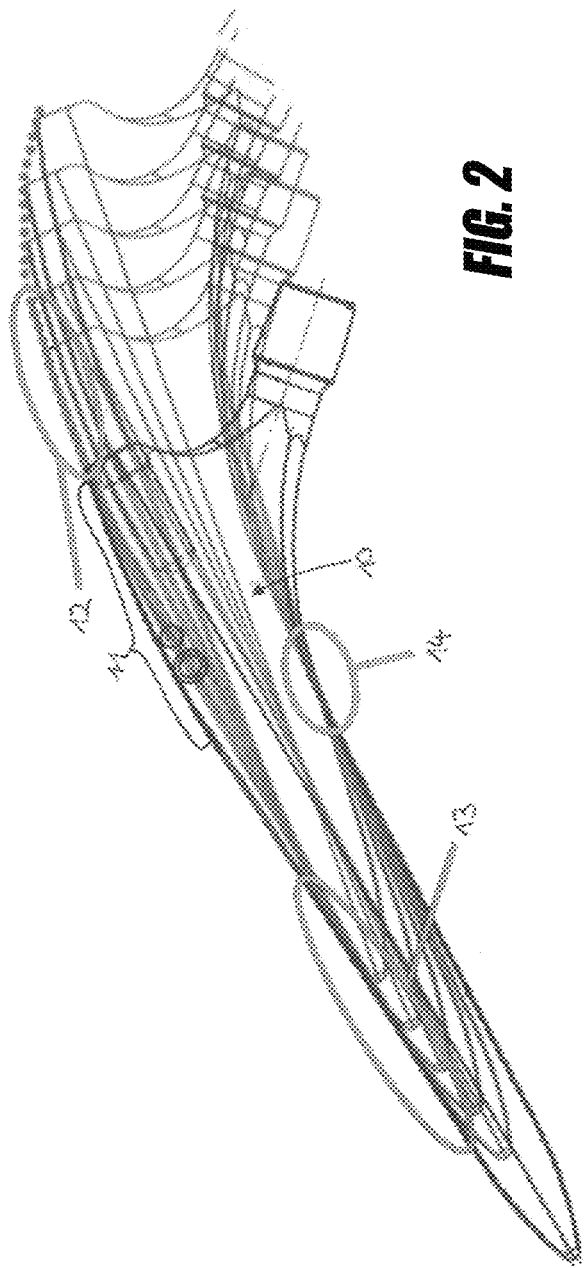
FIG. 2 depicts the path of the hip joint prosthesis upon entering a cavity.

A preferred shape of the convex proximal arcuate portion of a shaft stem comprises an arcuate portion that can be in the form of a "tractrix," which is described or defined by the proximal end of the lateral narrow side of the stem on introduction thereof (or of a corresponding rasp) into a complementary cavity in the femur while the contact between the lateral-distal and proximal-medial stem contour on the one hand and the associated boundary of the cavity on the other hand is maintained. The preferred shape of the proximal-lateral shoulder area is therefore derived from the guidance of the stem in the bony bed, as shown in FIG. 2. The lateral-proximal stem curvature 11 of the stem 10 corresponds to the curve 12 which is described by the proximal end of the lateral narrow side of the stem 10 on introduction thereof into a complementary cavity in the femur, on condition that the contact between the lateral-distal stem contour 13 and the proximal-medial stem contour 14 on the one hand and the associated boundary of the cavity (not shown herein) on the other hand is retained. A stem 10 constructed in accordance with one embodiment of the invention is otherwise shown in side view (ventral or dorsal) in FIG. 1, and moreover in comparison with a conventional blade-like stem according to FIG. 6 or EP 0 240 815 B1. FIG. 1 shows some differences from the prior art. The lateral side of the trochanter wing 9 according to FIG. 6 has been trimmed in FIG. 1 as a result of the lateral-proximal arcuate portion 11 with the advantage that there is correspondingly less interference with the ridge of the trochanter and, in particular, muscle and tendon insertions are also less severely affected during implantation or formation of the cavity for the stem 10. The contact zones in the region of the so-called Shenton's arch (region 14 in FIG. 2) and at the lateral-distal end (region 13 in FIG. 2) describe an arc along the lateral shoulder. That arc is described by a polynomial (curve of the xth order). That curve can follow on continuously from the lateral-distal stem geometry; preferably, however, it forms an angle therewith. In any case, the lateral-proximal arcuate portion is so configured that over the entire introduction path of the distal straight stem portion the shoulder has contact with or generally constant spacing from the bone structure in the trochanter region. There is thus achieved an optimum, exactly fitting shoulder area with respect to the bony bed with gap-free seating or with a predetermined gap for cement, according to whether a cementless or cemented implantation is to be carried out.

Figure 7:
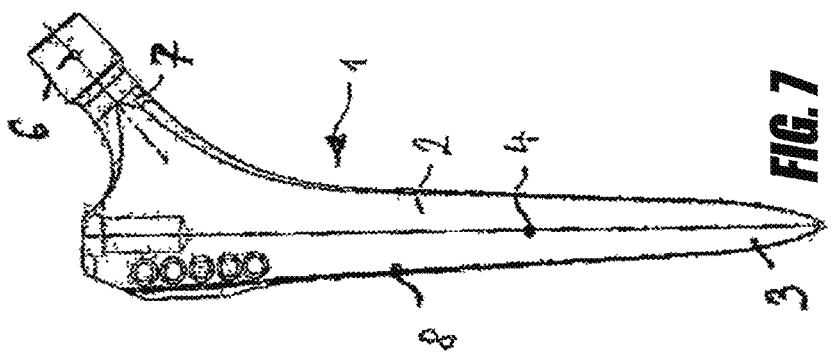
FIG. 7 depicts a schematic side view of another embodiment of a hip joint prosthesis.
Figure 3:
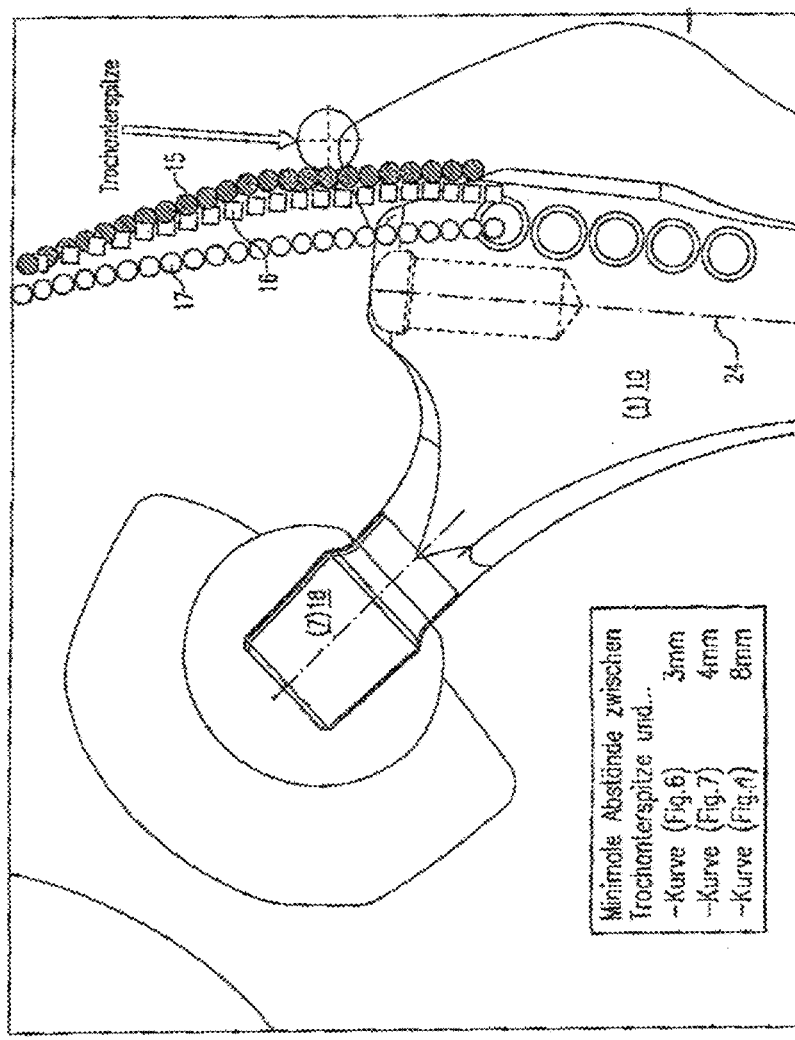
FIG. 3 depicts introduction paths of a proximal end of various hip joint prostheses.

In principle, it would also be possible to continue the lateral-distal straight portion in the proximal region in accordance with FIG. 7. That embodiment, however, is very much less protective of muscle and tendons than the embodiment according to the invention in accordance with FIG. 1. That can be seen very clearly especially from FIG. 3, which shows the introduction paths of the proximal end of the lateral narrow side of the stem for the versions in accordance with FIG. 6, FIG. 7 and FIG. 1. The introduction path 15 applies to the construction in accordance with FIG. 6 (prior art). The introduction path 16 applies to the construction according to FIG. 7 and the introduction path 17 applies to the configuration according to the invention in accordance with FIG. 1. Accordingly, there is least interference with the trochanter in the case of the embodiment according to the invention.

Also with reference to FIG. 1, it should be pointed out that the Figure shows a blade-like stem 10 of a hip joint prosthesis for anchoring in the femur, the stem being constructed in accordance with an embodiment of the invention. The stem has a portion 19 comprising a prosthesis neck 18 on the one hand and a femur-anchoring portion 21 tapering towards a distal end 20 on the other hand, the lateral narrow side 22 of which comprises a distal straight portion 23 and a proximal arcuate portion 11, the straight portion 23 extending over a length $L_D$ of from 60% to 75% of the total length $L_G$ of the stem 10. In the embodiment shown, the lateral straight portion 23 can merge continuously into the lateral arcuate portion 11, that is to say it is tangential. As already mentioned, however, it is entirely acceptable and in accordance with the invention for that transition to comprise a discontinuity, and/or be obtuse-angled.

As already mentioned above, it is especially advantageous for the lateral arcuate portion 11 to be in the form of a kind of "tractrix" which is described or defined by the proximal end of the lateral narrow side of the stem 10 on introduction thereof into a complementary cavity in the femur while the contact between the lateral-distal and proximal-medial stem contour on the one hand and the associated boundary of the cavity on the other hand is maintained. In this respect reference is again made to FIG. 2.

Depending upon the size of the stem and the external conditions, the proximal arcuate portion 11 is preferably configured with a constant, however especially continuously or discontinuously changing radius of between 200 mm and 500 mm.

It has also proved practical for the proximal arcuate portion 11 to be configured with a radius that becomes increasingly larger continuously or discontinuously from distal to proximal.

The arcuate portion 11 can especially also be in the form of a hyperbolic, parabolic or elliptical portion such that towards the distal end of the arcuate portion the portion in question merges into the conical straight portion 23 at a predetermined point at which the tangent forms with the stem axis 24 an angle equal to half the cone angle.

In connection with the stem itself, it should also be mentioned that the anchoring portion widens conically over the length of the lateral-distal straight portion 23 starting from the distal end 20 in the direction of its longitudinal axis 24 either all round or only laterally-medially.

It should also be mentioned that the cross-section of the stem 10 is preferably rectangular, but may also be trapezoidal or rhombic.

The mentioned all-round conical widening of the anchoring portion 21 has a cone angle of about from 0.5° to 6°, especially about from 1° to 3°. In some embodiments the anchoring portion 21 can widen on only the ventral and/or dorsal side.

Figures 8A, 8B:
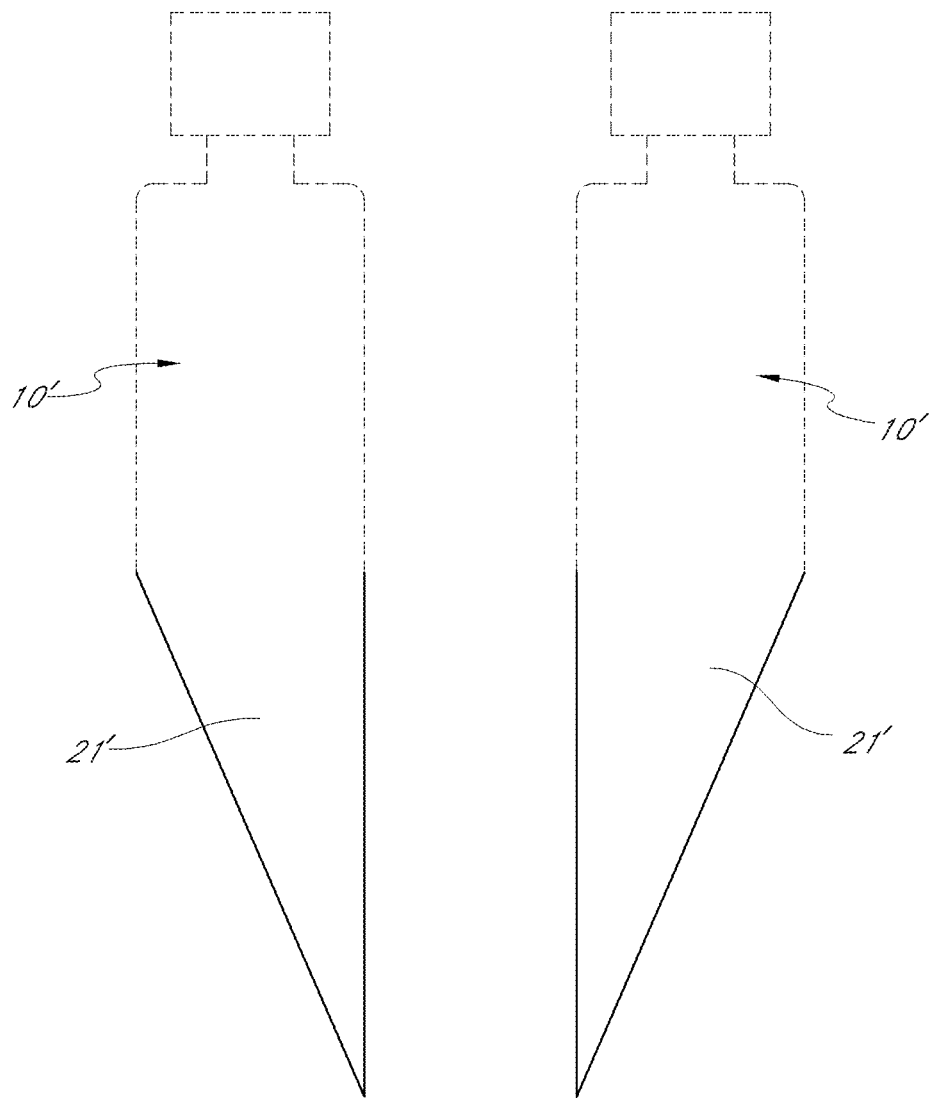
FIG. 8A depicts a schematic front view of another embodiment of a hip joint prosthesis.
FIG. 8B depicts a schematic front view of another embodiment of a hip joint prosthesis.

FIGS. 8A and 8B depict other non-limiting embodiments, where an anchoring portion 21' of a prosthesis stem 10' widens on the ventral or dorsal sides. FIG. 8A depicts this widening on the ventral side. FIG. 8B depicts this widening on the dorsal side.

All the features disclosed in the application documents are claimed as being important to the invention, insofar as they are novel over the prior art individually or in combination.

REFERENCE NUMERALS

Figure 6:
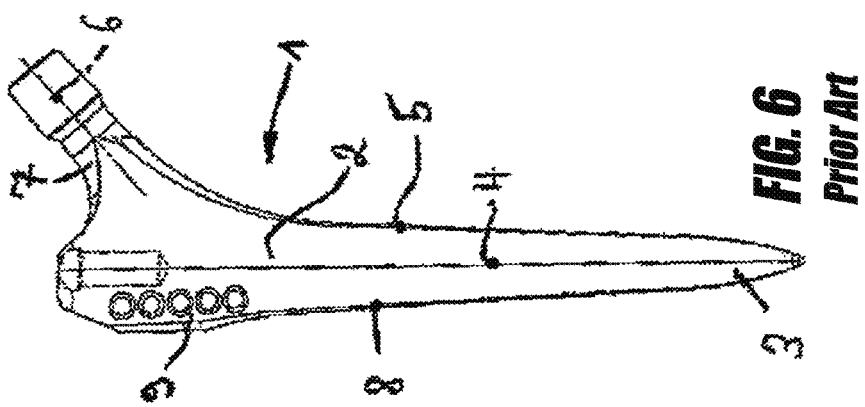
FIG. 6 depicts a prior art hip joint prosthesis

Prior Art:
1 stem
2 femur-anchoring portion
3 distal end
4 longitudinal axis
5 medial narrow side
6 prosthesis neck axis
7 prosthesis neck
8 lateral narrow side
9 trochanter wing
Invention:
10 stem
11 proximal-lateral stem curvature (lateral-proximal arcuate portion)
12 curve
13 lateral-distal stem contour
14 proximal-medial stem contour
15 introduction curve for stem according to FIG. 6
16 introduction curve for stem according to FIG. 7
17 introduction curve for stem according to FIG. 1
18 prosthesis neck
19 portion
20 distal end
21 femur-anchoring portion
22 lateral narrow side
23 distal-lateral straight portion
24 stem axis

What is claimed is:

1. A hip joint prosthesis stem for anchoring in a femur, comprising:
a femur-anchoring portion having a proximal end, a distal end, and a total length extending from the proximal end to the distal end, said femur-anchoring portion having a lateral narrow side comprising a distal straight portion extending from a location adjacent the distal end of the femur-anchoring portion, and a proximal arcuate portion extending from the distal straight portion to a location adjacent the proximal end of the femur-anchoring portion, the proximal arcuate portion having a radius of curvature that becomes increasingly smaller in a distal-to-proximal direction.

2. The prosthesis of claim 1, wherein the distal straight portion merges tangentially into the proximal arcuate portion.

3. The prosthesis of claim 1, wherein the distal straight portion merges into the proximal arcuate portion at an obtuse angle.

4. The prosthesis of claim 1, wherein the proximal arcuate portion is adapted to engage the trochanter region of a complementary cavity in the femur throughout introduction of the prosthesis stem into the complementary cavity.

5. The prosthesis of claim 1, wherein the proximal arcuate portion is adapted to have a constant spacing from the trochanter region of a complementary cavity in the femur throughout introduction of the prosthesis stem into the complementary cavity.

6. The prosthesis of claim 1, wherein the distal straight portion extends over a length of the femur-anchoring portion from 60% to 75% of the total length; and
wherein the proximal arcuate portion extends over a length of the femur-anchoring portion from 25% to 40% of the total length.

7. The prosthesis of claim 1, wherein the proximal arcuate portion is adapted to engage or to be spaced a distance from a trochanter region of a complementary cavity of the femur upon introduction of the proximal arcuate portion into the complementary cavity of the femur at a first depth where a lateral-distal and proximal-medial portion of the stem are adapted to be in contact with a boundary of the complementary cavity of the femur; and
wherein the proximal arcuate portion is adapted to engage or to be spaced the distance from the trochanter region where the lateral-distal and proximal-medial portion of the stem are adapted to be in contact with a boundary of the cavity and where the stem is adapted to be introduced at a depth greater than the first depth.

8. The prosthesis of claim 1, wherein the proximal arcuate portion extends along a tractrix curvature.

9. The prosthesis of claim 1, wherein the radius of curvature of the proximal arcuate portion continuously changes in the distal-to-proximal direction from the distal straight portion to the location adjacent the proximal end of the femur-anchoring portion.

10. The prosthesis of claim 1, wherein the radius of curvature of the proximal arcuate portion continuously decreases in the distal-to-proximal direction from the distal straight portion to the location adjacent the proximal end of the femur-anchoring portion.

11. A hip joint prosthesis stem for anchoring in a femur, comprising:
a prosthesis neck portion; and
a femur-anchoring portion extending from the prosthesis neck portion and having a proximal end, a distal end, and a total length extending from the proximal end to the distal end, the femur-anchoring portion tapering towards the distal end, the femur-anchoring portion comprising a lateral narrow side comprising a distal straight portion extending from a location adjacent the distal end and a proximal arcuate portion extending from the distal straight portion to a location adjacent the proximal end, the proximal arcuate portion having a radius of curvature that becomes increasingly smaller in a distal-to-proximal direction.

12. The prosthesis of claim 11, wherein said distal straight portion merges into said proximal arcuate portion at an obtuse angle.

13. The prosthesis stem of claim 11, wherein the distal straight portion merges tangentially into the proximal arcuate portion.

14. The prosthesis of claim 11, wherein the proximal arcuate portion extends over a length of the femur-anchoring portion from 25% to 40% of the total length.

15. The prosthesis of claim 11, wherein said proximal arcuate portion is adapted to engage or have a constant spacing from a trochanter region of a complementary cavity in the femur throughout introduction of the prosthesis stem into the complementary cavity in the femur while contact between a lateral-distal and proximal-medial stem contour and an associated boundary of the complementary cavity in the femur is adapted to be maintained.

16. The prosthesis of claim 11, wherein the proximal arcuate portion extends along a tractrix curvature.

17. The prosthesis of claim 11, wherein the radius of curvature of the proximal arcuate portion continuously changes in the distal-to-proximal direction from the distal straight portion to the location adjacent the proximal end of the femur-anchoring portion.

18. The prosthesis of claim 11, wherein the radius of curvature of the proximal arcuate portion continuously decreases in the distal-to-proximal direction from the distal straight portion to the location adjacent the proximal end of the femur-anchoring portion.

19. A hip joint prosthesis stem for anchoring in a femur, comprising:
a prosthesis neck portion;
a femur-anchoring portion extending from the prosthesis neck portion and having a proximal end, a distal end, and a total length extending from the proximal end to the distal end, the femur-anchoring portion tapering towards the distal end, the femur-anchoring portion comprising a lateral narrow side comprising a distal straight portion extending from a location adjacent the distal end and over a length of from 60% to 75% of the total length, the lateral narrow side further comprising a proximal arcuate portion extending from the distal straight portion to a location adjacent the proximal end of the femur-anchoring portion, the proximal arcuate portion having a radius of curvature that becomes increasingly smaller in a distal-to-proximal direction, and wherein the proximal arcuate portion extends over a length of the femur-anchoring portion of from 25% to 40% of the total length.

20. The prosthesis of claim 19, wherein said distal straight portion merges into said proximal arcuate portion at an obtuse angle.

21. The prosthesis of claim 19, wherein said anchoring portion widens over the lateral-distal straight portion starting from the distal end toward the proximal end.

22. The prosthesis of claim 21, wherein said anchoring portion widens about its entire circumference.

23. The prosthesis of claim 22, wherein said anchoring portion widens conically.

24. The prosthesis of claim 21, wherein said anchoring portion widens only in the lateral-medial direction.

25. The prosthesis of claim 21, wherein said anchoring portion widens with a taper angle between about 0.5° to about 6°.

26. The prosthesis of claim 25, wherein said taper angle is defined only on the ventral side of the anchoring portion.

27. The prosthesis of claim 25, wherein said taper angle is defined only on the dorsal side of the anchoring portion.

28. The prosthesis of claim 25, wherein the anchoring portion widens with a taper angle between about 1° to about 3°.

29. The prosthesis of claim 19, wherein the cross-section of said stem is selected from the group consisting of rectangular, trapezoidal and rhombic.

30. The prosthesis of claim 19, wherein the proximal arcuate portion is adapted to engage the trochanter region of a complementary cavity in the femur throughout introduction of the prosthesis stem into the complementary cavity.

31. The prosthesis of claim 19, wherein the proximal arcuate portion is adapted to have a constant spacing from the trochanter region of a complementary cavity in the femur throughout introduction of the prosthesis stem into the complementary cavity.

32. The prosthesis of claim 19, wherein said proximal arcuate portion comprises a changing radius of curvature between 200 mm and 500 mm.

33. The prosthesis of claim 19, wherein said proximal arcuate portion is adapted to engage or have a constant spacing from a trochanter region of a complementary cavity in the femur throughout introduction of the prosthesis stem into the complementary cavity in the femur while contact between a lateral-distal and proximal-medial stem contour and an associated boundary of the complementary cavity in the femur is adapted to be maintained.

34. The prosthesis of claim 19, wherein the proximal arcuate portion extends along a tractrix curvature.

35. The prosthesis of claim 19, wherein the radius of curvature of the proximal arcuate portion continuously decreases in the distal-to-proximal direction from the distal straight portion to the location adjacent the proximal end of the femur-anchoring portion.

36. A hip joint prosthesis stem for anchoring in a femur, comprising:
a prosthesis neck portion;
a femur-anchoring portion extending from the prosthesis neck portion and having a proximal end, a distal end, and a total length extending from the proximal end to the distal end, the femur-anchoring portion tapering towards the distal end, the femur-anchoring portion comprising a lateral narrow side comprising a distal straight portion extending from a location adjacent the distal end and over a length of from 60% to 75% of the total length, the lateral narrow side further comprising a proximal arcuate portion extending from the distal straight portion to a location adjacent the proximal end of the femur-anchoring portion, the proximal arcuate portion having a radius of curvature that becomes increasingly smaller in a distal-to-proximal direction, and wherein the distal straight portion merges tangentially into the proximal arcuate portion.

37. A hip joint prosthesis stem for anchoring in a femur, comprising:
a prosthesis neck portion;
a femur-anchoring portion extending from the prosthesis neck portion and having a proximal end, a distal end, and a total length extending from the proximal end to the distal end, the femur-anchoring portion tapering towards the distal end, the femur-anchoring portion comprising a lateral narrow side comprising a distal straight portion extending from a location adjacent the distal end and over a length of from 60% to 75% of the total length, the lateral narrow side further comprising a proximal arcuate portion extending from the distal straight portion to a location adjacent the proximal end of the femur-anchoring portion, the proximal arcuate portion having a radius of curvature that becomes increasingly smaller in a distal-to-proximal direction, and wherein the radius of curvature of the proximal arcuate portion continuously changes in the distal-to-proximal direction from the distal straight portion to the location adjacent the proximal end of the femur-anchoring portion.

* * * * *